US00PP33864P2

(12) United States Plant Patent
Hanes

(10) Patent No.: US PP33,864 P2
(45) Date of Patent: Jan. 11, 2022

(54) ***PELARGONIUM* PLANT NAMED 'PEQZ0085'**

(50) Latin Name: ***Pelargonium* interspecific**
Varietal Denomination: PEQZ0085

(71) Applicant: SYNGENTA CROP PROTECTION AG, Basel (CH)

(72) Inventor: Mitchell E. Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/363,221

(22) Filed: Jun. 30, 2021

(51) Int. Cl.
*A01H 5/02* (2018.01)
*A01H 6/42* (2018.01)

(52) U.S. Cl.
USPC ..... Plt./328
CPC ..... *A01H 6/425* (2018.05)

(58) Field of Classification Search
USPC ..... Plt./328
CPC ..... A01H 6/425; A01H 5/02
See application file for complete search history.

*Primary Examiner* — Keith O. Robinson
(74) *Attorney, Agent, or Firm* — Dale Skalla

(57) ABSTRACT

A new *Pelargonium* plant named 'PEQZ0085' particularly distinguished by the deep coral pink petals with a darker spot. The plant is very heat and drought tolerant with green leave, continuous color through the most extreme summer heat and is freely flowering.

1 Drawing Sheet

Latin name of the genus and species of the plant claimed: *Pelargonium* interspecific.

Varietal denomination: 'PEQZ0085'.

BACKGROUND OF THE NEW PLANT

The present invention comprises a new *Pelargonium*, botanically known as *Pelargonium* interspecific, and hereinafter referred to by the variety name 'PEQZ0085'.

'PEQZ0085' is a product of a planned breeding program. The new cultivar 'PEQZ0085' has inflorescences that are deep coral pink with a darker spot (splash) at the base of each petal. The plant is green foliage, very heat and drought tolerant with continuous color through the most extreme summer heat and is freely flowering.

'PEQZ0085' originates from a hybridization in a controlled breeding program made in January 2017, in a greenhouse in Guatemala. The female parent was an unpatented, proprietary plant of *P.* interspecific parentage, identified as '11391-1' with a single flower form and with a coral splash flower color.

The male parent of unpatented, proprietary plant of *P.* interspecific parentage, identified as '11530-3' a semidouble flower with rose splash color. The resultant seed was sown in June 2017.

'PEQZ0085' was selected as one flowering plant within the progeny of the stated cross in September 2017 in a greenhouse in Gilroy, Calif.

The first act of asexual reproduction of 'PEQZ0085' was accomplished when vegetative cuttings were propagated from the initial selection in October 2017 in a greenhouse in Gilroy, Calif.

BRIEF SUMMARY OF INVENTION

Horticultural examination of plants grown from cuttings of the plant initiated in December 2010 in Gilroy, Calif., and continuing thereafter, has demonstrated that the combination of characteristics as herein disclosed for 'PEQZ0085' are firmly fixed and are retained through successive generations of asexual reproduction.

'PEQZ0085' has not been observed under all possible environmental conditions. The phenotype may vary significantly with variations in environment such as temperature, light intensity, and day length.

A Plant Breeder's Right for this cultivar has not yet been applied for. 'PEQZ0085' has not been made publicly available prior to the effective filing date of this application, notwithstanding any disclosure that may have been made less than one year prior to the effective filing date of this application by the inventor or another who obtained 'PEQZ0085' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

Figure 1:
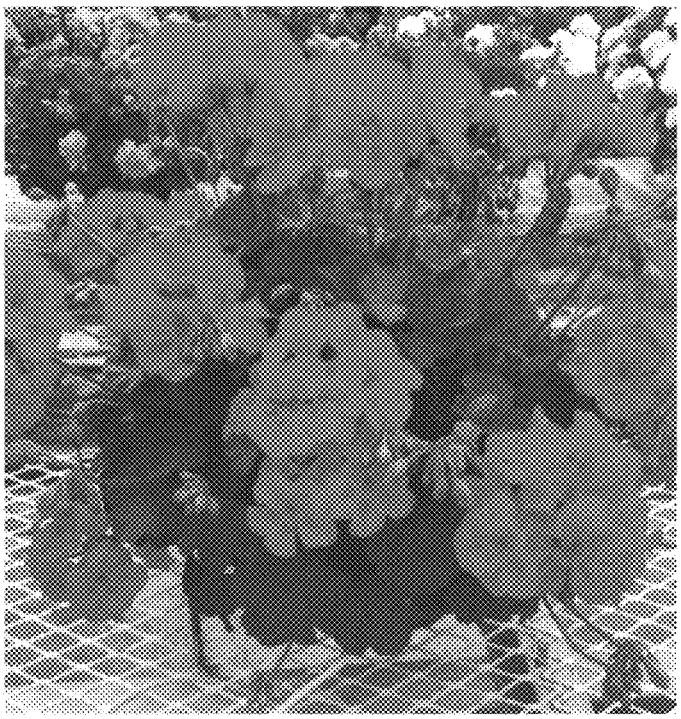
Figure 2:
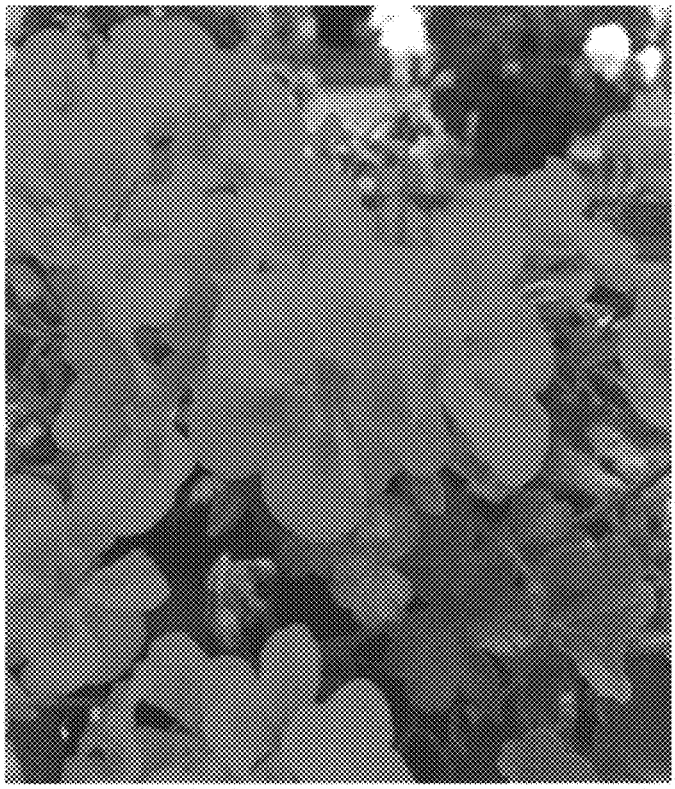

The accompanying photographic drawings show typical flower and foliage characteristics of 'PEQZ0085' with colors being as true as possible with an illustration of this type. The photographic drawings show in FIG. 1, 3 flowering plants of the new variety and in FIG. 2, a close-up of an inflorescence.

DETAILED BOTANICAL DESCRIPTION

The plant descriptions and measurements were taken in Gilroy, Calif. in June 2021 under natural light. These plants were approximately 20 weeks old and were grown in a 1 quart pots, in a greenhouse trial. The plants shown in the photographs were about 20 weeks old and were taken at the same time the plant patent data was collected.

Color references are made to The Royal Horticultural Society Colour Chart (R.H.S.) 2005.

TABLE 1

DIFFERENCES BETWEEN THE NEW VARIETY 'PEQZ0085' AND A MOST SIMILAR VARIETY

| | 'PEQZ0085' | 'Calliope Medium Mega Rose Splash', U.S. Plant Pat. No. 30,133 |
|---|---|---|
| Floret size: | Larger | Smaller |
| Flower bud | More elongated | More rounded |
| Plant growth | Rounded upright | Upright |

Plant:
*Form, growth and habit.*—Rounded upright habit, well branched plant, freely flowering.
*Plant height.*—17-20 cm.
*Plant height (inflorescence included).*—24-27 cm.
*Plant width.*—31-33.0 cm.
Roots:
*Number of days to initiate roots.*—15-18 days at about 22 degrees C.
*Number of days to produce a rooted cutting.*—21-23 days at 22 degrees C.
*Type.*—Fine, fibrous, free branching.
*Color.*—RHS N155B but whiter.
Foliage:
*Immature leaf, color upper surface.*—Closest to RHS 137 A.
*Immature leaf, lower surface.*—RHS 137B.
*Mature leaf, color upper surface.*—RHS 137A.
*Mature leaf, color lower surface.*—RHS 137B.
*Length.*—4.3 cm.
*Width.*—8.4 cm.
*Shape.*—Cordate.
*Base shape.*—Cordate.
*Apex shape.*—Acute.
*Margin.*—Slightly Dentate.
*Texture upper side.*—Hirsute.
*Texture lower side.*—Hirsute.
*Leaf zonation color.*—None.
*Color of veins, upper surface.*—RHS 137A becoming indistinct.
*Color of veins, lower surface.*—RHS 137C becoming indistinct.
*Pattern of veining.*—Palmate.
*Petiole color.*—RHS 137C.
*Petiole length.*—5-5.5 cm.
*Diameter of petiole.*—0.3 cm.
*Texture.*—Pilose, hirsute, glandular hairs.
Stem:
*Quantity of branches.*—6-8.
*Color of stem.*—Between RHS 144A and RHS 144B.
*Length of stem.*—9-11 cm.
*Diameter.*—0.5-0.6 cm.
*Length of internodes.*—1.0-2.0 cm.
*Texture.*—Sparsely hirsute, Pilose, glandular hairs.
Peduncle:
*Color of peduncle.*—RHS 137C.
*Length of peduncle.*—11-15 cm.
*Peduncle diameter.*—0.3-0.35 cm.
*Texture.*—Hirsute, glandular hairs.
Pedicel:
*Color of pedicel.*—RHS 137C at base and RHS 64B/C on upper half.
*Length of pedicel.*—2.4 cm.
*Diameter of pedicel.*—1.5-0.2 cm.
*Texture.*—Sparsely pilose, glandular hairs.
Bud (just before opening):
*Color.*—Closest to RHS 52A.
*Length.*—8 mm.
*Width.*—7 mm.
*Shape.*—Elliptical.
Inflorescence:
*Type.*—Umbel; semi-spherical or nearly semi-spherical.
*Lastingness of individual flowers.*—7-9 days at 18° C. temperature.
*Number of inflorescences per plant.*—15 with 18 immature umbels in various stages.
*Fragrance.*—None.
*Umbel diameter.*—8.5-10 cm.
*Umbel depth.*—5 cm.
Corolla:
*Form.*—Single.
*Number of petals.*—7-8.
*Diameter of flower.*—4.5 cm.
*Depth of flower.*—1.8 cm.
*Color upper petals, upper surface.*—Closest to RHS N57B/C.
*Color upper petals, lower surface.*—Closest to RHS N57A.
*Length of upper petals.*—2.5 cm.
*Width of upper petals.*—1.8 cm.
*Color lower petals, upper surface.*—Closest to RHS N57B/C.
*Color lower petals, lower surface.*—Closest to RHS N57A.
*Length of lower petals.*—2.2 cm.
*Width of lower petals.*—1.6 cm.
*Petal shape.*—Obovate to spathulate.
*Apex shape.*—Rounded.
*Margin.*—Entire.
*Base.*—Attenuate.
*Petal texture.*—Papillose on both surfaces.
Calyx:
*Number of sepals.*—5.
*Color of sepals.*—RHS 144B.
*Length of sepals.*—8 mm.
*Width of sepals.*—3-4 mm.
*Sepal shape.*—Lanceolate to linear.
*Apex shape.*—Acute.
*Margins.*—Mostly fused.
*Texture, upper surface.*—Glabrous.
*Lower surface.*—Glandular hairs, hirsute.
Reproductive organs:
Gynoecium:
*Pistil.*—1.
*Length.*—1.1 cm.
*Style color.*—Closest to RHS 53D with white to follow.
*Style length.*—0.7 cm.
*Stigma color.*—Closest to RHS 53D.
*Ovary color.*—Between RHS 144A and RHS 144B.
*Ovary length.*—0.5 cm.
*Ovary diameter.*—0.2 cm.
Androecium:
*Number of stamens.*—8-10.
*Color of filaments.*—RHS N57B with RHS N155C basally.
*Length filaments* 0.6 cm.
*Anther color.*—RHS N57B with RHS155C to follow.
*Length of anthers.*—0.2 cm.
*Color of pollen.*—RHS 58C.
*Pollen amount.*—Sparse.
*Fertility/seed set.*—Has not been determined to date.
*Disease/pest resistance.*—Has not been determined to date.

What is claimed is:

1. A new and distinct variety of *Pelargonium* plant named 'PEQZ0085' substantially as illustrated and described herein.

* * * * *